United States Patent [19]

Liese, Jr.

[11] Patent Number: 4,912,740

[45] Date of Patent: Mar. 27, 1990

[54] INTRAORAL DENTAL RADIOGRAPHIC FILM PACKET IMPROVEMENT

[75] Inventor: Elmer W. Liese, Jr., Rochester, N.Y.

[73] Assignee: Eastman Kodak Company, Rochester, N.Y.

[21] Appl. No.: 234,443

[22] Filed: Aug. 19, 1988

[51] Int. Cl.[4] .......................... A61B 6/14; G03B 42/02
[52] U.S. Cl. ..................................... 378/169; 378/168; 206/455
[58] Field of Search ................. 378/168, 169; 206/455

[56] References Cited

U.S. PATENT DOCUMENTS

| | | | |
|---|---|---|---|
| D. 290,652 | 6/1987 | Simpson | D24/16 |
| D. 291,917 | 9/1987 | Simpson | D24/2 |
| 1,537,925 | 5/1925 | Bolin | 378/169 |
| 1,631,497 | 6/1927 | Marler | 378/169 |
| 1,783,467 | 12/1930 | Goldacker et al. | 378/169 |
| 1,994,579 | 3/1935 | Hodgson | 250/168 |
| 2,084,092 | 6/1937 | Kenney | 250/168 |
| 3,443,093 | 5/1969 | Lindenmuth et al. | 378/169 |
| 3,551,673 | 12/1970 | Siegel | 378/168 |
| 3,936,643 | 2/1976 | Toner | 378/168 |
| 4,626,216 | 12/1986 | Strong-Grainger | 433/229 |
| 4,791,657 | 12/1988 | Kirsch et al. | 378/169 |
| 4,805,201 | 2/1989 | Strong-Grainger | 378/168 |

FOREIGN PATENT DOCUMENTS 56-50524 11/1981 Japan .

Primary Examiner—Craig E. Church
Assistant Examiner—John C. Freeman
Attorney, Agent, or Firm—William C. Dixon

[57] ABSTRACT

A comfort-enhancing improvement upon a known dental film packet having sensitized film and protective opaque sheets enclosed by a light-tight envelope that includes an opposed pair of generally parallel walls covering the sheets, those walls being joined together along facing marginal areas thereof surrounding the sheets so as to define a main body portion and a perimetric edge portion of the envelope. The improvement comprises a pliant bead of substantially non-porous, non-toxic, polymeric elastomeric material, preferably a silicone resin, that is molded in situ around at least part of the perimetric edge portion to encapsulate that part of the edge portion with such material and thereby provide the encapsulated part with a softer, smoother, and more rounded peripheral surface. In the molding process illustrated, the polymeric elastomeric material is injected under pressure into a mold peripheral-channel of circular cross section surrounding the envelope edge portion; and the mold is then heated for optimal, low-temperature, controlled curing of the bead formed therein.

11 Claims, 4 Drawing Sheets

INTRAORAL DENTAL RADIOGRAPHIC FILM PACKET IMPROVEMENT

BACKGROUND OF THE INVENTION

1. Field of the Invention

The present invention relates generally to intraoral dental radiographic film packets, and particularly to an improvement therein that renders them more comfortable for the patient.

2. Description of the Prior Art

The prior art is replete with dental film packets of the type referred to above. Examples may be found in the following documents:

U.S. Pat. No. 1,631,497—Discloses a dental x-ray film package comprising superposed sensitized and protective sheets and a soft, pliable beading that embraces their edges to hold the sheets together and to render the package more comfortable in use; the beading may be of molded rubber or a stretched rubber band cemented in place.

U.S. Pat. No. 3,443,093—Discloses a dental x-ray film package comprising sensitized and protective sheets superposed within a readily openable sealed envelope of substantially uniform overall thickness.

U.S. Pat. No. 4,626,216—Discloses a resiliant pad (made of foamed ethylene vinyl acetate) that is folded over, and adhered to, one edge and two corners of a dental x-ray film packet, to enhance comfort and to facilitate positioning in the patient's mouth.

While such film packages and associated pads may have sufficed for their respective purposes, there has remained a persistant need for a dental film packet improvement that would efficiently render the packet markedly more comfortable when operatively positioned inside a patient's mouth. This need has long existed, especially for the particular type of film packet disclosed in the cited U.S. Pat. No. 3,443,093. The squared-off edge defining the perimeter of that packet has been a continuing cause of considerable discomfort for some patients whenever that edge has been pressed into sensitive tissues of the mouth.

A common approach to cushioning that edge has been to attach a soft pad around it, as disclosed, for example, in the cited U.S. Pat. No. 4,626,216. One drawback to adding a cushioning pad has been the resulting increase in overall film package size, which may make it difficult to position the package correctly in the patient's mouth, and may cause stacking and gating problems when loaded into commonly used film packet dispensing devices. Another drawback of the typical cushioning pad has been that the open-cell, or foamed, material used therein to enhance its cushioning effect absorbs patient saliva, which may be contaminated with contagious viruses.

Although dental x-ray film packets of the type disclosed in U.S. Pat. No. 3,443,093 have been widely used for more than twenty years, the long-recognized need to ameliorate discomfort in some patients, in a practical and efficient manner, without adversely increasing overall film packet size, and without using highly porous, saliva-absorbing materials, has not been met until the advent of this invention.

SUMMARY OF THE INVENTION

A primary object of this invention has been to meet the foregoing need for such a comfort-enhancing film packet improvement. Another object has been to do so in a totally reliable, yet practical and economical, manner. Those and other objects have been achieved by the invention herein disclosed and claimed.

This invention finds utility as an improvement upon a known intraoral dental radiographic film packet having sensitized film and protective opaque sheets enclosed by a light-tight envelope that includes an opposed pair of generally parallel walls covering the sheets, those walls being joined together along facing marginal areas thereof surrounding the sheets so as to define a main body portion and a perimetric edge portion of the envelope. The improvement of this invention, which effectively renders such a packet far more comfortable in use, comprises a pliant bead that is permanently integral with the perimetric edge portion of the envelope and composed of a substantially non-porous, non-toxic, polymeric elastomeric material molded, in situ, around at least part of the perimetric edge portion to encapsulate at least part of the edge portion with such material and thereby provide that part with a softer, smoother, and more rounded peripheral surface.

This invention, and its objects and advantages, will become more apparent in the detailed description of the preferred embodiment thereof presented hereinbelow.

BRIEF DESCRIPTION OF THE DRAWINGS

In the detailed description of the preferred embodiment of this invention presented below, reference is made to the accompanying drawings, wherein like reference characters denote like elements, and wherein.

DESCRIPTION OF THE PREFERRED EMBODIMENT

Because certain parts of intraoral dental radiographic film packets are well known, the following description is directed in particular to those elements forming, cooperating directly with, or relating to, this invention. Elements not specifically shown or described herein are selectable from those known in the relevant art.

Figure 1:
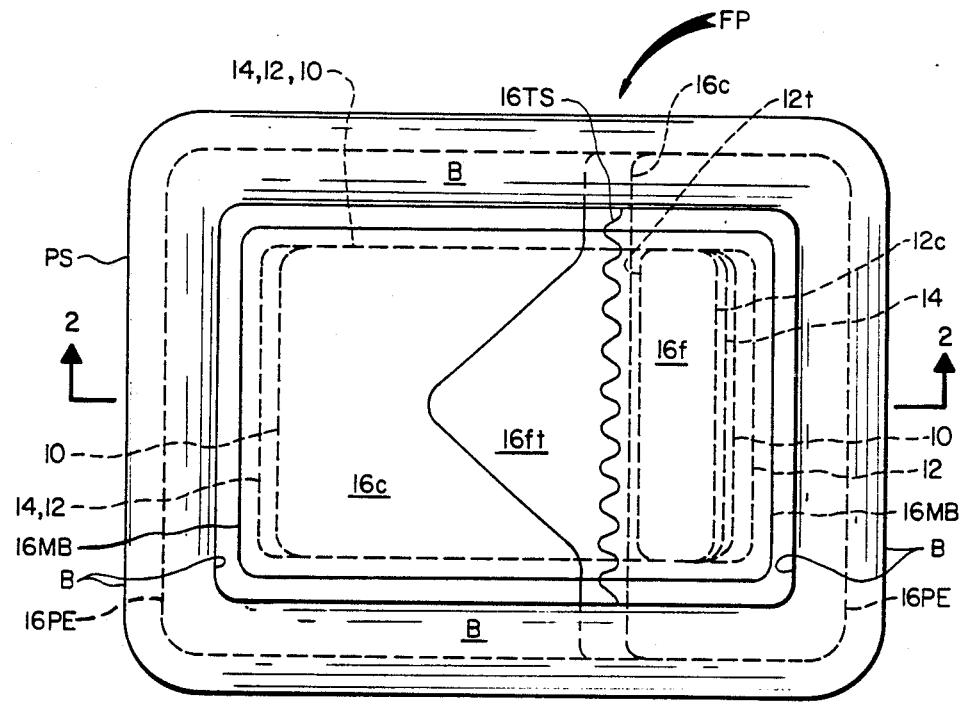
FIG. 1 is a top-plan view of a known intraoral dental radiographic film packet as improved in accordance with the preferred embodiment of this invention, showing the improved packet in its fully assembled and closed condition.
Figure 2:
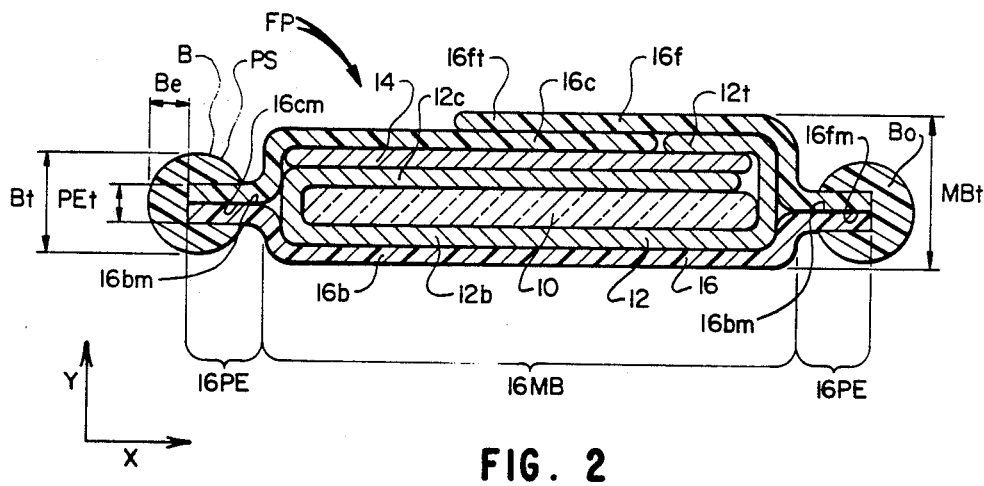
FIG. 2 is a cross-sectional elevation of the improved packet depicted in FIG. 1, taken along line 2—2 therein but showing its principal components greatly exaggerated in thickness for clarity of illustration.

FIGS. 1 and 2 illustrate an intraoral dental radiographic film packet of a known type, disclosed in the aforementioned U.S. Pat. No. 3,443,093, as improved in accordance with the preferred embodiment of this invention. The packet, designated generally by the letters FP, comprises a sheet of x-ray film 10 having a sensitive emulsion on one or both sides (as is well known in the art); a folded black paper wrapper 12; a sheet of metal foil 14 substantially the same shape and size as the film sheet 10; and an enclosing envelope 16, preferably plastic, within which the foregoing components are arranged as shown and sealed. As is well known, the envelope 16 may be made of a duplex plastic sheet, i.e., a sheet of white plastic on the outside laminated to a sheet of black plastic on the inside. The plastic preferred for the envelope is polyvinylchloride, although polyethylene, Pliofilm, cryovac, or other plastic films or combinations of plastics might also suffice. The white outside surface of the envelope may be matte, glossy, or embossed. The metal foil sheet 14 preferably is made of lead, but any metal that absorbs x-rays satisfactorily for dental radiographic purposes may be used.

In the assembled film packet, as shown in FIG. 2, the paper wrapper 12 comprises a base section 12b underlying film sheet 10, a folded-over cover section 12c overlying film sheet 10, and a folded-over tab section 12t overlying the right-hand end portions of film sheet 10 and cover section 12c. It will be seen that metal foil sheet 14 lies between cover section 12c and tab section 12t. The plastic envelope 16 comprises a bottom wall 16b underlying the paper wrapper base section 12b, a cover section 16c overlying the metal foil sheet 14, and a flap section 16f overlying both the paper wrapper tab section 12t and the envelope cover section 16c. Cover section 16c and flap section 16f together form the top wall of the envelope. As shown in FIG. 1, the left-hand end portion of envelope flap section 16f is triangular in shape, to form a tab end 16ft of the flap section. Flap section 16f is tack-sealed to cover section 16c, transversely of the envelope as indicated by the undulated line 16TS. The envelope bottom wall 16b includes an upward-facing marginal area 16bm which is sealed to an opposing downward-facing marginal area 16cm of cover section 16c and an opposing downward-facing marginal area 16fm of flap section 16f. The seal may be provided in any suitable manner, e.g., by heat, ultrasonics, or an adhesive. To open the packet for processing film sheet 10 after its exposure, the technician first grasps the unsealed tab end 16ft of flap section 16f and then pulls the flap section upwardly, so as to break the transverse seal 16TS and rip open the seal between marginal areas 16fm and 16bm. With the envelope thus opened, the technician then grasps paper wrapper tab section 12t and pulls paper wrapper 12 out of the envelope with film sheet 10 riding between wrapper base and cover sections 12b and 12c.

With the envelope bottom wall 16b joined to the top wall cover and flap sections 16c and 16f along their opposing marginal areas as described, the envelope may be viewed as comprising a main body portion 16MB surrounded by a perimetric edge portion 16PE, as shown most clearly in FIG. 2. It will be seen that the squared-off peripheral edge of perimetric edge portion 16PE includes relatively sharp top and bottom corners, which have caused considerable discomfort when pressed against sensitive tissues of some patients' mouths. The present invention provides an efficient and reliable means for ameliorating such discomfort.

As a comfort-enhancing improvement upon a film packet of the type thus far described, this invention comprises a pliant bead B of substantially non-porous, non-toxic, polymeric elastomeric material molded, in situ, around at least part of the envelope perimetric edge portion 16PE, to encapsulate at least part of the edge portion with such material and thereby provide the encapsulated part of that portion with a softer, smoother, and more rounded peripheral surface PS.

In accordance with the preferred embodiment illustrated in FIG. 1, the pliant bead B is continuous around all of, and thus completely surrounds, the perimetric edge portion 16PE. It should be understood, however, that this invention also contemplates alternative embodiments (not shown) wherein the bead may be discontinuous, and thus encapsulates only part(s) of the perimetric edge portion. For example, such a bead could be provided only around the envelope corners and/or along one or more of the envelope sides.

Although not necessary for the purposes of this invention, the bead preferably has a substantially circular cross section Bo taken in a plane perpendicular to the envelope bottom and top walls, as shown in FIG. 2. That circular cross section Bo has a diametral thickness Bt as measured in a first direction Y perpendicular to the envelope walls. The perimetric edge portion 16PE, around which bead B is molded, has an edge thickness PEt as measured in the first direction Y perpendicular to the walls. Preferably, the bead diametral thickness Bt is at least twice the edge thickness PEt. The envelope main body portion 16MB has an overall thickness MBt as measured in first direction Y perpendicular to the walls. Preferably, the bead diametral thickness Bt is no greater than the main body portion overall thickness MBt. Also, the bead extends outwardly beyond the perimetric edge portion 16PE in a second direction X parallel with the envelope walls by an amount Be that is no greater than one-half the bead diametral thickness Bt.

In a number of successful test samples of such a packet, the envelope main body portion overall thickness MBt, as measured in first direction Y, ranged from about 0.056 inches (1.422 mm) to about 0.061 inches (1.549 mm), with a mean of about 0.058 inches (1.483 mm); and the envelope perimetric edge portion edge thickness PEt, as measured in first direction Y, ranged from about 0.006 inches (0.157 mm) to about 0.012 inches (0.310 mm), with a mean of about 0.010 inches (0.246 mm). Optimally, for packets having such dimensions, their bead thickness Bt, as measured in first direction Y, should range only from about 0.012 inches (0.315 mm) to about 0.061 inches (1.549 mm); and their bead extension Be, as measured in second direction X, should not exceed about 0.031 inches (0.787 mm).

Polymeric elastomeric materials suitable for molding pliant bead B include certain polyurethane and, preferably, silicone materials. In the foregoing test samples, the bead was molded from a silicone resin. Optimally, the bead peripheral surface PS should have a hardness falling between 20 and 40 Shore A (using a "Type A Shore Durometer" as specified in the *Standard Test Method for RUBBER PROPERTY—DUROMETER HARDNESS*, American Society for Testing and Materials Designation D 2240-85).

Figure 3:
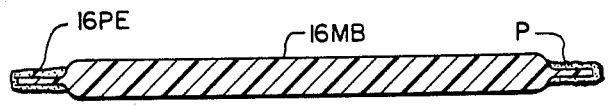
FIGS. 3 and 4 are simplified cross-sectional elevations of the known packet shown in FIGS. 1 and 2 as modified to illustrate preparatory steps toward achieving the preferred embodiment of this invention.
Figure 4:
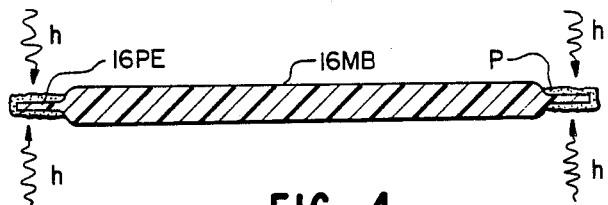

The method used for molding pliant bead B around perimetric edge portion 16PE in the above-mentioned samples will now be described with reference to FIGS. 3-11. First, as depicted in FIG. 3, a coating of silicone primer P was applied to the external surfaces of perimetric edge portion 16PE. The particular primer selected was General Electric SS4179 Silicone Primer. Next, as indicated schematically in FIG. 4, the primed packet was allowed to cure for one (1) hour (60 minutes), a period which may be shortened upon suitable application of heat h to the affected surfaces.

Figure 5:
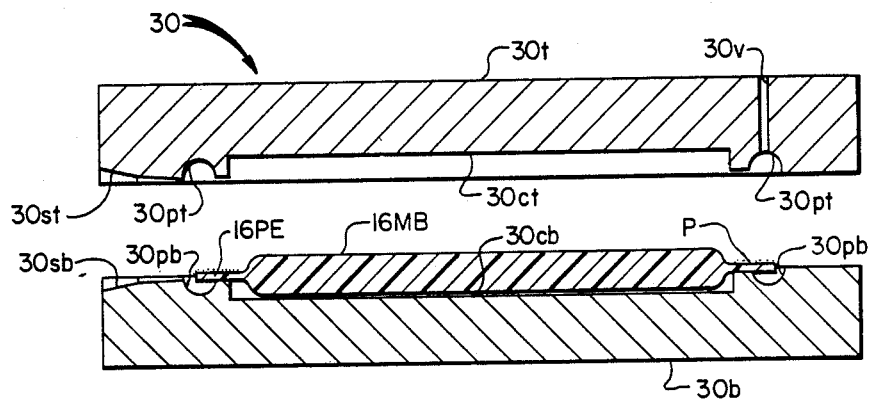
FIGS. 5, 6, 9, 10, and 11 are cross-sectional elevations of the packet of FIGS. 3 and 4 and apparatus associated therewith in succeeding steps of a method for achieving the preferred embodiment of this invention.
Figure 6:
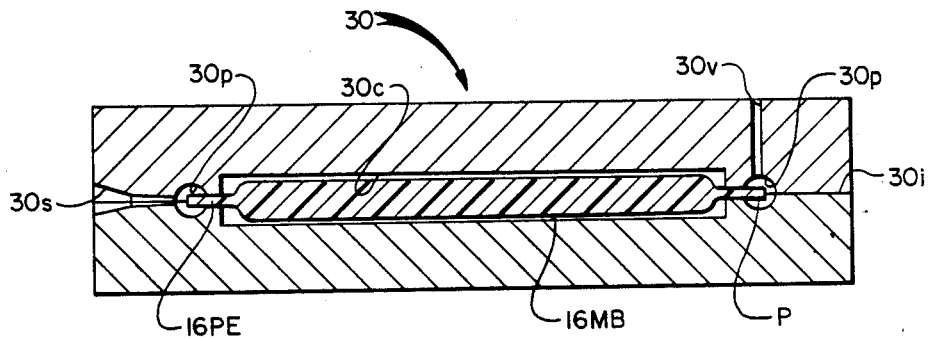
Figure 8:
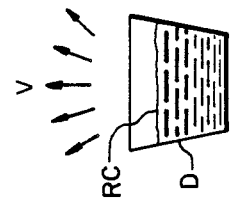
FIGS. 7 and 8 are schematic views illustrating further preparatory steps toward achieving the preferred embodiment of this invention.

As illustrated in FIG. 5, the primed and cured packet was then operatively positioned in a mold 30 comprising a bottom section 30b and a top section 30t. When the bottom and top mold sections 30b and 30t are brought together as shown in FIG. 6, they define a central cavity 30c, which is adapted to receive the envelope main body portion 16MB, and a peripheral channel 30p, which surrounds the central cavity and is adapted to receive the envelope perimetric edge portion 16PE. As indicated in FIG. 5, central cavity 30c comprises bottom and top portions thereof 30cb and 30ct located in bottom and top mold sections 30b and 30t respectively. Similarly, peripheral channel 30p comprises bottom and top portions thereof 30pb and 30pt located in bottom and top mold sections 30b and 30t respectively. A sprue 30s is provided in mold 30 for admitting the polymeric elastomeric bead forming material to peripheral channel 30p. Sprue 30s comprises bottom and top portions thereof 30sb and 30st located in bottom and top mold sections 30b and 30t respectively. Also provided in top mold section 30t is a vent 30v leading from peripheral channel top portion 30pt to the mold top section exterior.

FIG. 5 illustrates mold 30 in an opened condition, with the primed and cured packet operatively positioned on mold bottom section 30b so that its main body portion 16MB rests in central cavity bottom portion 30cb and its perimetric edge portion 16PE extends into peripheral channel bottom portion 30pb. With the packet so positioned on mold bottom section 30b, the mold top section 30t was brought down and secured to the bottom section 30b, thus closing mold 30 about the packet so as to seal central cavity 30c from peripheral channel 30p, all as shown in FIG. 6. The closed mold is depicted in FIG. 6 as having the bottom and top portions of its central cavity, peripheral channel, and sprue concentrically disposed relative to the interface 30i of its bottom and top mold sections. The loaded mold was then ready for injection of the polymeric elastomeric bead forming material.

Figure 7:
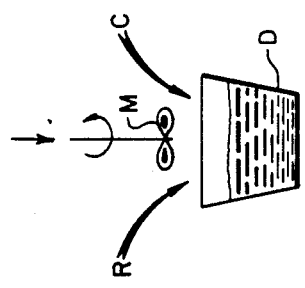

As pictured schematically in FIG. 7, fifty (50) grams of General Electric RTV700 Silicone Resin, having the chemical name Polydimethylsiloxane and designated herein by the letter R, were placed into a mixing dish D. Five (5) grams of General Electric Beta 1 Silicone Catalyst, designated herein by the letter C, were then added to the silicone resin in dish D and mixed thoroughly by mixing means M for two (2) minutes. Next, as portrayed schematically in FIG. 8, the resin-catalyst mixture, designated RC, was evacuated under a vacuum V of twenty-nine (29) inches (73.66 cm) of mercury for two (2) minutes after collapse of the initial head.

Figure 9:
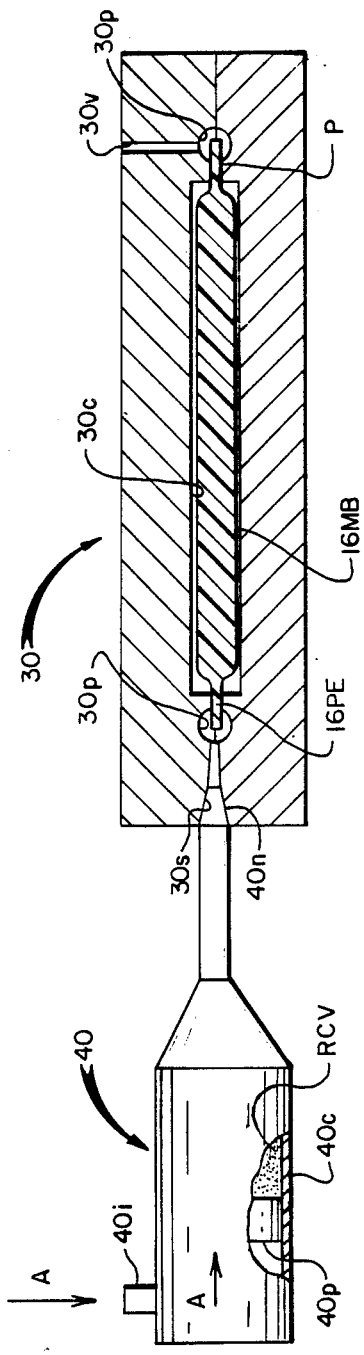

Referring now to FIG. 9, the evacuated resin-catalyst mixture, designated RCV, was loaded into a six-ounce (177 ml) polyethylene Semco Gun caulk tube, which served as a molding material injector 40. The nozzle 40n of injector 40 was then placed into an injection port at the outer end of mold sprue 30s, whereupon the mold was filled with mixture RCV, under thirty (30) pounds per square inch (2.1 kilograms per square centimeter) of air pressure, until the injected mixture became visible at the top of mold vent 30v.

As depicted schematically in FIG. 9, the mentioned air pressure came from a source A thereof, through an inlet 40i to the injector cylinder 40c, and then acted upon injector piston 40p to move the piston to the right, thereby forcing the mixture RCV through nozzle 40n and sprue 30s and thus into the peripheral channel 30p.

While the mentioned 30 pounds per square inch (2.1 kilograms per square centimeter) of air pressure proved effective for the samples made, other pressures, e.g., from about 25 to about 35 pounds per square inch (1.8 to 2.5 kilograms per square centimeter), should also be satisfactory.

Figure 10:
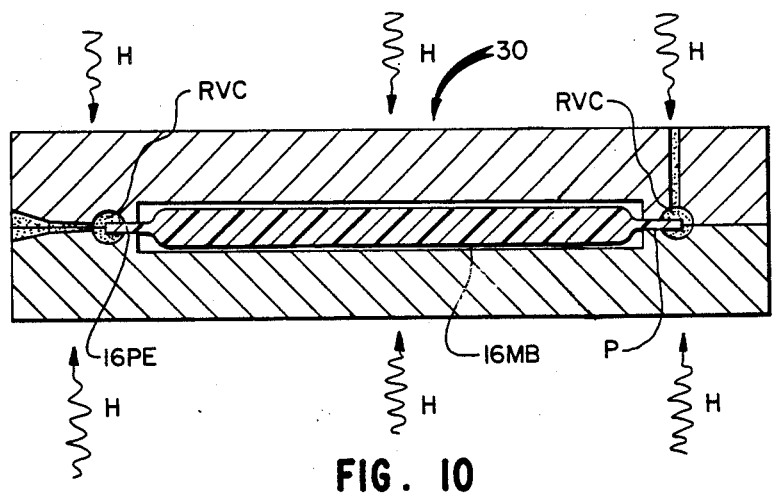
Figure 11:
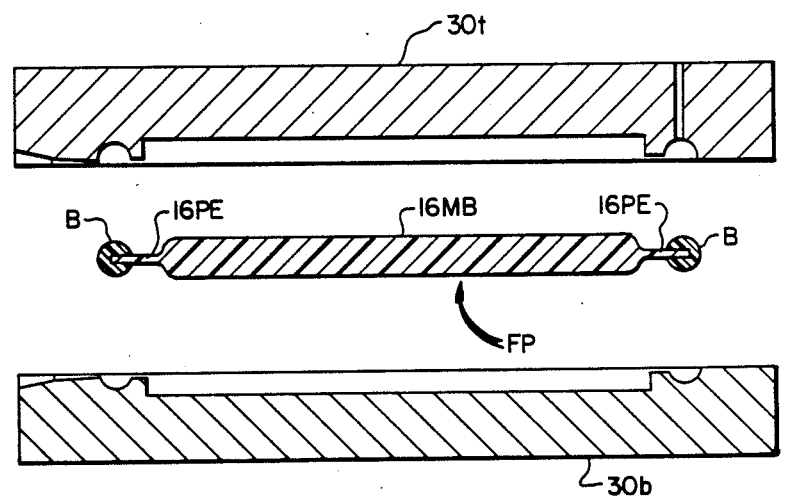

As depicted schematically in FIG. 10, the filled mold 30 was then subjected to a source of heat H, heated to a curing temperature of ninety (90) degrees Fahrenheit (32.2 degrees Celsius), and maintained at that temperature for a curing time of three (3) hours (180 minutes). While the foregoing curing temperature and curing time selected for these samples proved successful, other temperatures and times, e.g., from about 85 to about 95 degrees Fahrenheit (29.4 to 35.0 degrees Celsius) and from about 150 to about 200 minutes, should also be satisfactory. After the needed curing time had passed, the mold was opened by separating its bottom and top sections, as indicated in FIG. 11, and the packet was removed as improved by the pliant bead of silicone resin material molded in situ around its perimetric edge portion. It will be noted that the mold peripheral channel 30p is so configured as to impart a substantially circular cross section to any bead formed therein.

It has been found that such a pliant bead of substantially non-porous, non-toxic, polymeric elastomeric material, as efficiently molded in situ around the packet perimetric edge portion, has proven most effective in reliably cushioning sensitive mouth tissues from painful effects of an otherwise sharply cornered packet edge. The film packet improvement of this invention has thus successfully fulfilled a widespread, long-recognized, but hitherto-unresolved need for a markedly more comfortable intraoral dental radiographic film packet.

The present invention has now been described in detail with particular reference to its preferred embodiment as illustrated herein. It will be understood, however, that variations and modifications can be effected within the spirit and scope of this invention.

I claim:

1. In combination with an intraoral dental radiographic film packet having sensitized film and protective opaque sheets enclosed by a light-tight envelope that includes an opposed pair of generally parallel walls covering the sheets, said walls being joined together along facing marginal areas thereof surrounding the sheets so as to define a main body portion and a perimetric edge portion of said envelope, an improvement rendering the packet more comfortable in use, said improvement comprising a pliant bead that is permanently integral with said perimetric edge portion of said envelope and composed of a substantially non-porous, non-toxic, polymeric elastomeric material molded, in situ, around at least part of said perimetric edge portion, to encapsulate at least part of the edge portion with such material so as to provide that part with a softer, smoother, and more rounded peripheral surface.

2. An intraoral dental radiographic film packet improvement as claimed in claim 1 wherein said bead is continuous around all of, and thus completely surrounds, said perimetric edge portion of said envelope.

3. An intraoral dental radiographic film packet improvement as claimed in claim 1 wherein said bead has a substantially circular cross section perpendicular to said walls.

4. An intraoral dental radiographic film packet improvement as claimed in claim 3 wherein said circular cross section of said bead has a diametral thickness as measured perpendicular to said walls, wherein said perimetric edge portion of said envelope has an edge thickness as measured perpendicular to said walls, and wherein said diametral thickness is at least twice said edge thickness.

5. An intraoral dental radiographic film packet improvement as claimed in claim 3 wherein said circular cross section of said bead has a diametral thickness as measured perpendicular to said walls, wherein said main body portion of said envelope has an overall thickness as measured perpendicular to said walls, and wherein said diametral thickness is no greater than said overall thickness.

6. An intraoral dental radiographic film packet improvement as claimed in claim 3 wherein said circular cross section of said bead has a diametral thickness as measured perpendicular to said walls, and wherein said bead extends outwardly beyond said perimetric edge portion in a direction parallel with said walls by an amount no greater than one-half said diametral thickness.

7. An intraoral dental radiographic film packet improvement as claimed in claim 1 wherein said main body portion of said envelope has an overall thickness dimension as measured in a first direction perpendicular to said walls, wherein said perimetric edge portion of said envelope has an edge thickness dimension as measured in said first direction, wherein said bead molded around said edge portion has a bead thickness dimension as measured in said first direction, wherein said bead thickness dimension is at least twice said edge thickness dimension but no greater than said overall thickness dimension, and wherein said bead extends outwardly beyond said edge portion in a second direction parallel with said walls by an amount no greater than one-half said bead thickness dimension.

8. An intraoral dental radiographic film packet improvement as claimed in claim 1 wherein said main body portion of said envelope has an overall thickness ranging from about 0.056 inches (1.422 mm) to about 0.061 inches (1.549 mm), wherein said perimetric edge portion of said envelope has an edge thickness ranging from about 0.006 inches (0.157 mm) to about 0.012 inches (0.310 mm), wherein said bead on said edge portion has a bead thickness ranging from about 0.012 inches (0.315 mm) to about 0.061 inches (1.549 mm), and wherein said bead extends laterally beyond said edge portion by an amount not exceeding 0.031 inches (0.787 mm).

9. An intraoral dental radiographic film packet improvement as claimed in claim 1 wherein said polymeric elastomeric material comprises one of a silicone material and a polyurethane material.

10. An intraoral dental radiographic film packet improvement as claimed in claim 9 wherein said polymeric elastomeric material comprises a silicone resin.

11. An intraoral dental radiographic film packet improvement as claimed in claim 1 wherein said peripheral surface has a hardness of 20 to 40 Shore A.

* * * * *